US00PP29596P3

(12) United States Plant Patent
Rijk

(10) Patent No.: US PP29,596 P3
(45) Date of Patent: Aug. 14, 2018

(54) ***BEGONIA* PLANT NAMED 'FIBEGUNFIKI'**

(50) Latin Name: *Begonia hybrida*
Varietal Denomination: Fibegunfiki

(71) Applicant: FIDES B.V., De Lier (NL)

(72) Inventor: Nadine Rijk, De Lier (NL)

(73) Assignee: Dümmen Group B.V., De Lier (NL)

( * ) Notice: Subject to any disclaimer, the term of this patent is extended or adjusted under 35 U.S.C. 154(b) by 63 days.

(21) Appl. No.: 14/999,903

(22) Filed: Jul. 14, 2016

(65) Prior Publication Data

US 2018/0020600 P1 Jan. 18, 2018

(51) Int. Cl.
*A01H 5/02* (2018.01)

(52) U.S. Cl.
USPC ..... Plt./343
CPC ..... *A01H 5/0238* (2013.01)

(58) Field of Classification Search
USPC ..... Plt./343, 348, 349
CPC ..... A01H 5/0238; A01H 5/05; A01H 5/00; A01H 5/02
See application file for complete search history.

(56) References Cited

U.S. PATENT DOCUMENTS

PP27,485 P2 * 12/2016 Rijk ..... A01H 5/0238
Plt./343

OTHER PUBLICATIONS

Galema's Greenhouse 2016 Spring Catalog, retrieved on Nov. 8, 2017, retrieved from the Internet at http://www.galemas.com/2016SpringCatalogWEB.pdf, 2 introductory pages, pp. 1, 11 and 2 back pages total of 6 pages (Year: 2016).*

Issuu Catalog Dummen Orange 2015-2016 retrieved on Nov. 8, 2017, retrieved from the Internet at https://issuu.com/bepplersrl/docs/catalog_d_mmen_orange_2015-2016, cover page, pp. 51 and 195 (Year: 2015).*

* cited by examiner

*Primary Examiner* — June Hwu
(74) *Attorney, Agent, or Firm* — C. A. Whealy

(57) ABSTRACT

A new and distinct cultivar of *Begonia* plant named 'Fibegunfiki', characterized by its upright to spreading and mounded plant habit; relatively compact; freely basal branching habit; dark green-colored leaves; freely and continuously flowering habit; and semi-double flowers that are deep pink in color.

2 Drawing Sheets

Botanical designation: *Begonia hybrida.*
Cultivar denomination: 'FIBEGUNFIKI'.

BACKGROUND OF THE INVENTION

The present invention relates to a new and distinct cultivar of *Begonia* plant, botanically known as *Begonia hybrida*, and hereinafter referred to by the name 'Fibegunfiki'.

The new *Begonia* plant is a product of a planned breeding program conducted by the Inventor in Aalsmeer, The Netherlands. The objective of the breeding program was to develop new freely branching and flowering *Begonia* plants with unique and attractive flower colors.

The new *Begonia* plant originated from a cross-pollination made by the Inventor in 2013 of a proprietary selection of *Begonia hybrida* identified as code number BG-1458, not patented, as the female, or seed, parent and a proprietary selection of *Begonia hybrida* identified as code number BG08-00182-002, not patented, as the male, or pollen, parent. The new *Begonia* plant was discovered and selected by the Inventor as a single flowering plant from within the progeny of the stated cross-pollination in a controlled greenhouse environment in Aalsmeer, The Netherlands in 2013.

Asexual reproduction of the new *Begonia* plant by vegetative tip cuttings in a controlled greenhouse environment in Aalsmeer, The Netherlands since 2013 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Fibegunfiki'. These characteristics in combination distinguish 'Fibegunfiki' as a new and distinct *Begonia* plant:

1. Upright to spreading and mounded plant habit; relatively compact.
2. Freely basal branching habit.
3. Dark green-colored leaves.
4. Freely and continuously flowering habit.
5. Semi-double flowers that are deep pink in color.

Plants of the new *Begonia* can be compared to plants of the proprietary parent selections. Plants of the new *Begonia* differ primarily from plants of the parent selections in uniformity as plants of the new *Begonia* are more uniform than plants of the parent selections. In addition, plants of the new *Begonia* are more freely flowering than plants of the parent selections.

Plants of the new *Begonia* can be compared to plants of *Begonia hybrida* 'Filuckstr', disclosed in U.S. Plant Pat. No. 27,485. In side-by-side comparisons, plants of the new *Begonia* differ primarily from plants of 'Filuckstr' in the following characteristics:

1. Plants of the new *Begonia* are more compact than plants of 'Filuckstr'.
2. Plants of the new *Begonia* have larger leaves than plants of 'Filuckstr'.
3. Plants of the new *Begonia* have larger male flowers than plants of 'Filuckstr'.
4. Plants of the new *Begonia* and 'Filuckstr' differ in flower color as plants of 'Filuckstr' have yellow-colored flowers with apricot-colored margins.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet is a side perspective view of a typical flowering plant of 'Fibegunfiki' grown in a container.

The photograph on the second sheet is a close-up view of a typical flowering plant of 'Fibegunfiki'.

DETAILED BOTANICAL DESCRIPTION

Plants used for the aforementioned photographs and following observations and measurements were grown in 12-cm containers during the summer in a glass-covered greenhouse in Rheinberg, Germany. During the production of the plants, day temperatures ranged from 17° C. to 30° C. and night temperatures ranged from 10° C. to 20° C. Plants were eight weeks old when the photograph and the description were taken. In the following description, color references are made to The Royal Horticultural Society Colour Chart, 2007 Edition, except where general terms of ordinary dictionary significance are used.

Botanical classification: *Begonia hybrida* 'Fibegunfiki'.

Parentage:

*Female, or seed, parent*.—Proprietary selection of *Begonia hybrida* identified as code number BG-1458, not patented.

*Male, or pollen, parent*.—Proprietary selection of *Begonia hybrida* identified as code number BG08-00182-002, not patented.

Propagation:

*Type*.—By vegetative tip cuttings.

*Time to initiate roots, summer*.—About 18 days at temperatures about 22° C. to 30° C.

*Time to initiate roots, winter*.—About 21 days at temperatures about 22° C. to 30° C.

*Time to produce a rooted young plant, summer*.—About 25 days at temperatures about 22° C. to 30° C.

*Time to produce a rooted young plant, winter*.—About 28 days at temperatures about 20° C. to 25° C.

*Root description*.—Medium in thickness, fibrous; typically whitish grey in color; actual color of the roots is dependent on substrate composition, water quality, fertilizer type and formulation, substrate temperature and physiological age of roots; plants of the new *Begonia* have not been observed to form tubers.

*Rooting habit*.—Moderately freely branching; medium density.

Plant description:

*Plant form and growth habit*.—Upright to spreading and mounded plant habit; relatively compact; pendulous with development; freely basal branching with about eight primary branches; moderately vigorous to vigorous growth habit.

*Plant height*.—About 20 cm.

*Plant width*.—About 26 cm.

*Lateral branch description*.—Length: About 8 cm to 12 cm. Diameter: About 6 mm. Internode length: About 5 mm to 20 mm. Texture: Smooth, glabrous. Color: Close to 199A.

*Leaf description*.—Arrangement: Alternate, simple. Length: About 13.5 cm. Width: About 5.5 cm. Shape: Ovate to lanceolate. Apex: Acute. Base: Cordate. Margin: Serrate. Texture, upper and lower surfaces: Smooth, glabrous. Venation pattern: Palmate; reticulate. Color: Developing and fully expanded leaves, upper surface: Darker than 147A; venation, close to N137B. Developing and fully expanded leaves, lower surface: Close to 181A; venation, close to 144B. Petioles: Length: About 5 cm. Diameter: About 5 mm. Texture, upper and lower surfaces: Smooth, glabrous. Color, upper and lower surfaces: Close to 199A.

Flower description:

*Flowering habit*.—Semi-double flowers arranged in axillary cymes; freely flowering habit with numerous flowers developing per plant; flowers pendulous and face outwardly to downwardly.

*Fragrance*.—None detected.

*Natural flowering season*.—Plants in full flower about eight weeks after planting; long flowering period, in the garden plants flower freely and continuously throughout the summer in Northern Europe and can be flowered year-round in greenhouses.

*Flower longevity*.—Individual flowers last about four weeks on the plant; flowers persistent.

*Number of flowers per inflorescence*.—About three.

*Inflorescence height (including peduncle)*.—About 8 cm.

*Inflorescence diameter*.—About 8 cm.

*Female flower buds*.—Length: About 3 cm. Diameter: About 2.5 cm. Shape: Ovoid. Texture: Smooth, glabrous. Color: Close to 142C and 49A.

*Female flowers*.—Diameter: About 4 cm. Depth (height): About 4 cm.

*Female flower tepals*.—Quantity per flower and arrangement: Typically five per flower arranged in a single whorl. Length: About 1.5 cm to 2 cm. Width: About 1.7 cm. Shape: Ovate. Apex: Acute. Base: Cordate. Margin: Entire. Texture, upper and lower surfaces: Smooth, glabrous. Color: When opening and fully opened, upper surface: Close to 52A. When opening and fully opened, lower surface: Close to 52B and N155A.

*Female flower tepaloids*.—None observed.

*Female flower pedicels*.—Length: About 2.5 cm. Diameter: About 2 mm. Aspect: About 90° from vertical. Strength: Moderately strong. Texture: Smooth, glabrous. Color: Close to 199A.

*Female flowers reproductive organs*.—Quantity of pistils per flower: Three. Pistil length: About 8 mm. Style length: About 7 mm. Style color: Close to 43B. Stigma shape: Curled. Stigma color: Close to 163B. Ovary color: Close to 143C and 46A. Fruits and seeds: Fruit and seed development have not been observed on plants of the new *Begonia*.

*Male flower buds*.—Length: About 7 mm. Diameter: About 9 mm. Shape: Ovoid. Texture: Smooth, glabrous. Color: Close to 142C and 49A.

*Male flowers*.—Diameter: About 7.5 cm. Depth (height): About 2.5 cm.

*Male flower tepals*.—Quantity per flower and arrangement: Typically about four to five arranged in a single whorl. Length: About 2.5 cm to 3.5 cm. Width: About 2.5 cm to 3.5 cm. Shape: Ovate. Apex: Acute. Base: Cordate. Margin: Entire. Texture, upper and lower surfaces: Smooth, glabrous. Color: When opening, upper surface: Close to 52A. When opening, lower surface: Close to 52B and N155A. Fully opened, upper surface: Close to 50A; color does not fade with development. Fully opened, lower surface: Close to 50B and N155A; color does not fade with development.

*Male flower tepaloids*.—Quantity per flower and arrangement: Typically about 16 arranged in several whorls. Length: About 2.5 cm. Width: About 1 cm to 1.5 cm. Shape: Oval, irregular. Apex: Acute. Base: Cordate. Margin: Entire. Texture, upper and lower surfaces: Smooth, glabrous. Color: When opening and fully opened, upper surface: Close to 50A and 23A; color does not fade with development. When opening and fully opened, lower surface: Close to 50B and N155A; color does not fade with development.

*Male flower pedicels*.—Length: About 3 cm. Diameter: About 2 mm. Aspect: About 90° from vertical. Strength: Moderately strong. Texture: Smooth, glabrous. Color: Close to 199A.

*Male flowers reproductive organs*.—None observed; all transformed into tepaloids.

Disease & pest resistance: Resistance to pathogens and pests common to *Begonia* plants has not been observed on plants of the new *Begonia*.

Temperature tolerance: Plants of the new *Begonia* have been observed to tolerate temperatures ranging from about 4° C. to about 35° C.

It is claimed:

1. A new and distinct *Begonia* plant named 'Fibegunfiki' as illustrated and described.

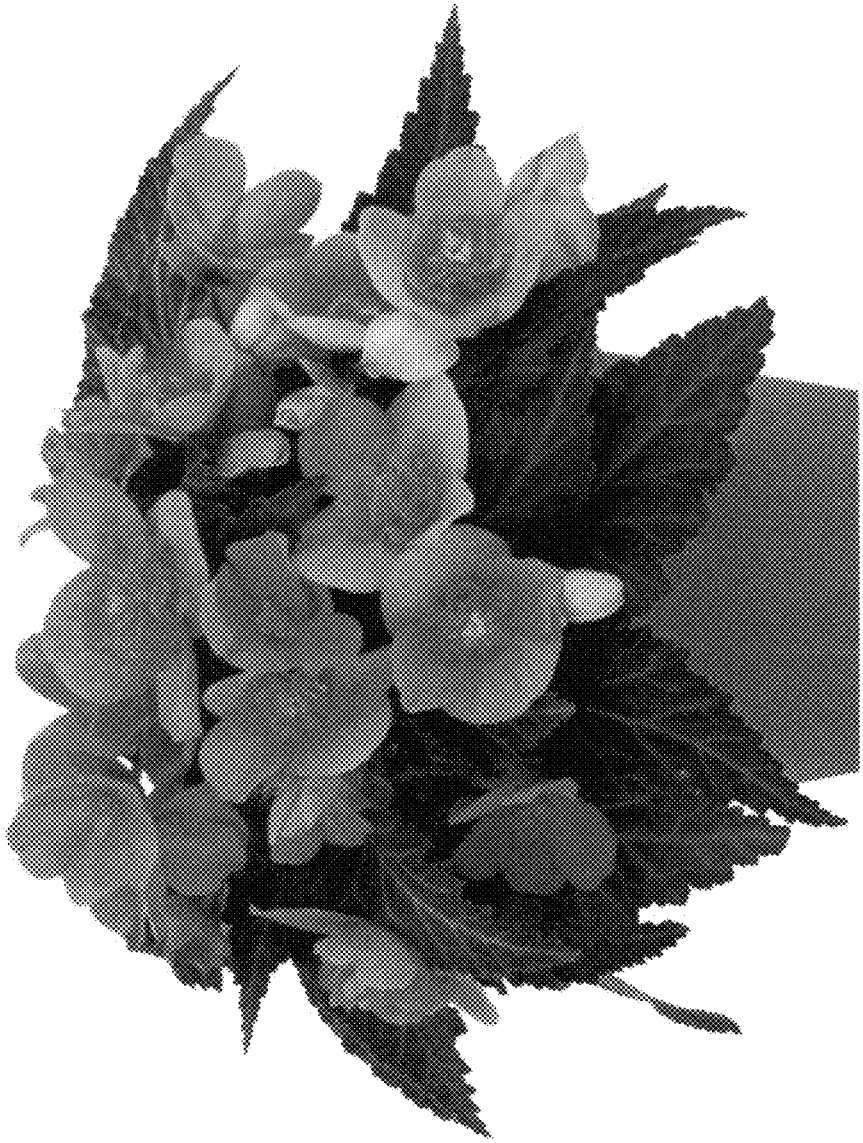

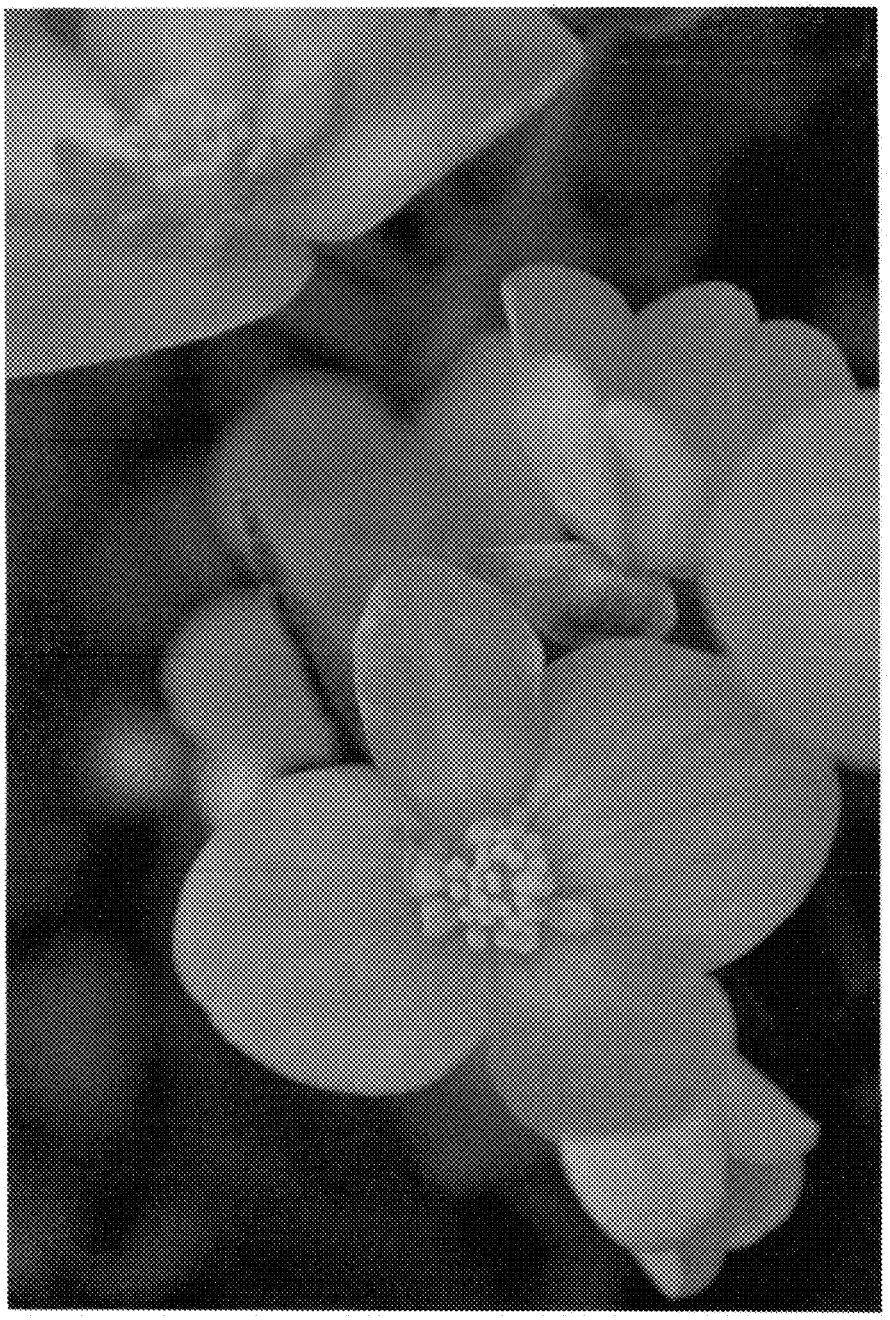

* * * * *